United States Patent
Shann et al.

(10) Patent No.: US 11,639,532 B2
(45) Date of Patent: May 2, 2023

(54) METHOD FOR INFLUENZA A VIRUS AND INFLUENZA B VIRUS DETECTION

(71) Applicant: CREDO DIAGNOSTICS BIOMEDICAL PTE. LTD., Singapore (SG)

(72) Inventors: Yih-Jyh Shann, New Taipei (TW); Chia-Hsin Su, New Taipei (TW)

(73) Assignee: CREDO DIAGNOSTICS BIOMEDICAL PTE. LTD., Singapore (SG)

(*) Notice: Subject to any disclaimer, the term of this patent is extended or adjusted under 35 U.S.C. 154(b) by 541 days.

(21) Appl. No.: 16/669,510

(22) Filed: Oct. 30, 2019

(65) Prior Publication Data

US 2020/0140963 A1    May 7, 2020

(30) Foreign Application Priority Data

Nov. 1, 2018 (TW) ................. 107138861

(51) Int. Cl.
*C12Q 1/70* (2006.01)
*C12Q 1/6888* (2018.01)
*G01N 33/58* (2006.01)

(52) U.S. Cl.
CPC ............. *C12Q 1/70* (2013.01); *C12Q 1/6888* (2013.01); *G01N 33/582* (2013.01)

(58) Field of Classification Search
CPC ....... C12Q 1/70; C12Q 1/6888; G01N 33/582
See application file for complete search history.

(56) References Cited

U.S. PATENT DOCUMENTS

| | | | | |
|---|---|---|---|---|
| 2004/0253582 | A1* | 12/2004 | Henrickson | C12Q 1/6851 435/5 |
| 2010/0330548 | A1* | 12/2010 | Detmer | C12Q 1/702 435/5 |
| 2014/0127674 | A1* | 5/2014 | Bradley | C12Q 1/701 435/5 |
| 2015/0133324 | A1* | 5/2015 | Zhang | C12Q 1/701 506/9 |
| 2017/0275712 | A1* | 9/2017 | Mokkapati | C12Q 1/701 |

FOREIGN PATENT DOCUMENTS

| | | |
|---|---|---|
| CN | 106555012 A | 4/2017 |
| TW | 201538734 A | 10/2015 |
| WO | 9716570 A1 | 5/1997 |
| WO | 2007095155 A2 | 8/2007 |
| WO | 2008079463 A2 | 7/2008 |
| WO | 2008140513 A1 | 11/2008 |
| WO | 2016028312 A1 | 2/2016 |

OTHER PUBLICATIONS

Zhang, Y. et al., Genotyping and detection of common avian and human origin-influenza viruses using a portable chemiluminescence imaging microarray, Springerplus, 2016, vol. 5, Article No. 1871, pp. 1-13.

Wu, L.-T. et al., Duplex Molecular Assay Intended for Point-of-Care Diagnosis of Influenza A/B Virus Infection, J. Clin. Microbiol., 2013, vol. 51, No. 9, pp. 3031-3038.

Selvaraju, S. B. et al., Evaluation of Three Influenza A and B Real-Time Reverse Transcription-PCR Assays and a New 2009 H1N1 Assy for Detection of Influenza Viruses, J. Clin. Microbiol., 2010, vol. 48, No. 11, pp. 3870-3875.

WHO information for the molecular detection of influenza viruses, WHO website, Jul. 2017, 4th revision, retrieved on Jul. 29, 2020, retrieved from the Internet, [URL] https://www.who.int/influenza/gisrs_laboratory/molecular_diagnosis/en/.

Shin, Y.K. et al., One-Step Multiplex Reverse-Transcriptase PCR for Detecting Pandemic (H1N1) 2009 Influenza Virus, J. Vet. Med. Sci., 2011,vol. 73, No. 1, pp. 55-63.

Jian Fan et al., "Detection of a novel avian influenza A (H7N9) virus in humans by multiplex one-step real-time RT-PCR assay" BMC Infectious Diseases, Biomed Central, Oct. 8, 2014, p. 541, vol. 14, No. 1, London, GB.

Stevenson J. et al., "The use of Armored RNA as a multi-purpose internal control for RT-PCR," Journal of Virological Methods, Elsevier BV, Jun. 1, 2008, , pp. 73-76, vol. 150, No. 1-2, NL.

European Patent Office Search Report for European Patent Application No. 19188685.2, dated Feb. 18, 2020, 9 pages.

\* cited by examiner

*Primary Examiner* — David C Thomas
(74) *Attorney, Agent, or Firm* — Sughrue Mion, PLLC

(57) ABSTRACT

The present invention discloses a method for detecting Influenza A virus and Influenza B virus in a suspected sample by detecting the matrix gene and the non-structural gene, respectively. The signals can be detected by a fluorescent detection system.

7 Claims, 5 Drawing Sheets

Specification includes a Sequence Listing.

METHOD FOR INFLUENZA A VIRUS AND INFLUENZA B VIRUS DETECTION

CROSS-REFERENCE TO RELATED APPLICATION

This application claims the benefit of Taiwan Patent Application No. 107138861, filed on Nov. 1, 2018, the contents of which is incorporated herein by reference.

FIELD OF THE INVENTION

This invention is rlated to a method for detecting Influenza A virus (Flu A) and Influenza B virus (Flu B) in a human tissue sample. In particular, for Flu A, the present invention provides primers, probes and other related reagents for detecting at least one of Influenza A subtype H1N1, H3N2, H5N1 and H7N9. For Flu B, the present invention provides primers, probes and other related reagents for detecting Influenza B virus.

BACKGROUND OF THE INVENTION

Influenza is commonly seen in local outbreaks or epidemics throughout the world. Epidemics may appear at any time but are usually concentrated in months of high humidity. They occur suddenly with little or no warning. The number of people affected can vary from a few hundred to hundreds of thousands. Epidemics may be short-lived, lasting days or weeks, but larger epidemics may last for months. Although influenza is a mild disease in most individuals, it is life threatening to elderly or debilitated individuals. Epidemics are responsible for large losses in productivity. The WHO commissioned an international network of communicating laboratories to monitor the antigenic changes in the infecting viruses and the spread of infection.

According to World Health Organization's research and data, Influenza A and B viruses accounted for the majority of influenza detections. Human Influenza A and B viruses cause seasonal epidemics of disease almost every winter in North America, East Asia, and South East Asia. Influenza type C infections generally cause a mild respiratory illness and are not thought to cause epidemics. Influenza D viruses only affect cattle and are not known to infect or cause illness in people.

Influenza A viruses are divided into subtypes based on two proteins on the surface of the virus: the hemagglutinin (H) and the neuraminidase (N). There are 18 different hemagglutinin subtypes and 11 different neuraminidase subtypes. Influenza A viruses can be further broken down into different strains. Influenza A virus belongs to the genus orthomyxovirus in the family of Orthomyxoviridae, which is a kind of ssRNA-enveloped virus with a helical symmetry. The genome of Influenza A virus is segmented, with 8 RNA fragments. There are four antigens present on Influenza A virus which are haemagglutinin (HA), neuraminidase (NA), nucleocapsid (NP) and the matrix (M) proteins. The NA is a type-specific antigen that occurs in 3 forms, A, B and C, which provides the basis for the classification of human influenza viruses. The matrix protein surrounds the nucleocapsid and makes up 35-45% of the particle mass. HA mediates the attachment of the virus to the cellular receptor. Neuraminidase molecules are present in lesser quantities in the envelope.

Influenza A virus is a major member of the human seasonal influenza, which can infect people of all ages and cause serious illnesses that can even lead to death. Seasonal influenza is an important global human respiratory disease caused by Influenza A virus, prevalent in tropical areas all year round, while in temperate regions occurs mainly in winter, with some seasonal epidemics features. Currently, there are two subtypes of Influenza A virus circulating in humans, which can lead to global pandemic infections, namely H1N1 and H3N2. Also, H5N1 and H7N9 are considered as important subtypes since infection with H5N1 and H7N9 in humans can cause severe disease and has a high mortality rate.

Influenza B virus is another genus in the virus family Orthomyxoviridae. The Influenza B virus genome is 14548 nucleotides long and consists of 8 segments of linear negative-sense, single-stranded RNA. The multipartite genome is encapsidated, each segment is in a separate nucleocapsid, and the nucleocapsids are surrounded by one envelope. Influenza B viruses are not divided into subtypes, but can be further broken down into lineages and strains. Currently there are two co-circulating lineages of the Influenza B virus based on the antigenic properties of the surface glycoprotein hemagglutinin. The lineages are termed B/Yamagata/16/88-like and B/Victoria/2/87-like viruses. The capsid of Influenza B virus is enveloped while its virion consists of an envelope, a matrix protein, a nucleoprotein complex, a nucleocapsid, and a polymerase complex.

Influenza A and B virus infections are spread via respiratory droplets. The virus particles bind to cells of the respiratory epithelium, which are rich in viral receptors. Neuraminidases present on the virus particles aid the infectious process by releasing virus particles which have been bound by the mucous present on the surface of epithelial cells. The typical symptoms of influenza appear after the infection and include marked fever, headache, photophobia, shivering, a dry cough, malaise, myalgia, and a dry tickling throat. The fever is continuous and lasts around 3 days. Though the symptoms and the treatments of Influenza B virus are similar to those of Influenza A virus, the chance of developing severe complications from Influenza B virus is lower than from Influenza A virus.

Influenza A subtypes H1N1, H3N2, H5N1, and H7N9 are all highly contagious and can cause severe complications. One of the Influenza A subtypes, H5N1, which is of particular concern because it mutates much more quickly than other Influenza A subtypes and Influenza B virus, has been proven to be highly pathogenic and can cause severe disease in men. Therefore, in order to monitor the mutation in real-time, it is important to make a distinction between Influenza A subtypes H1N1, H3N2, H5N1, and H7N9 versus Influenza B virus.

Nowadays, there are available RT-PCR assays for the detection of RNA of Influenza A and B viruses that provide the greatest sensitivity and specificity. Moreover, the PCR product can be sequenced for strain identification. The most sensitive and appreciated specimens are nasopharyngeal swabs. However, throat and nasal swabs are more commonly used given the difficulties involved in taking nasopharyngeal swabs.

In light of the above, it is necessary to develop an assay with high accuracy and stability for detecting at least one of Influenza A subtypes H1N1, H3N2, H5N1, and H7N9, and Influenza B virus in a suspected sample simultaneously.

SUMMARY OF THE INVENTION

The object of this present invention is to provide a detection method for detecting the presence of a matrix gene (hereinafter "M gene") of Influenza A subtypes H1N1, H3N2, H5N1, or H7N9 in a suspected sample, as well as for detecting the presence of a non-structural gene (hereinafter "NS gene") of Influenza B virus in the suspected sample simultaneously. To be more precise, if a suspected sample contains at least one of Influenza A subtype H1N1, H3N2, H5N1, or H7N9, then it would be detected by the present invention. If a suspected sample contains at least one strain of Influenza B virus, it would be detected by the present invention. Also, if a suspected sample contains at least one of Influenza A subtype H1N1, H3N2, H5N1, and Influenza B virus, then it would be detected separately by the present invention.

The object of the present invention, in particular, is to provide designated primers and probes for detecting the presence of Influenza A subtypes H1N1, H3N2, H5N1, and H7N9, and Influenza B virus in a suspected sample, respectively. The designated probes and primers are specific to Influenza A subtypes H1N1, H3N2, H5N1, and H7N9, and Influenza B virus. A template-dependent polymerase with ability of exonuclease hydrolysis is also included in this process. This object is achieved according to the present invention by a method for the detection of the presence of at least one of Influenza A subtype H1N1, H3N2, H5N1, and H7N9, and/or Influenza B virus in a suspected sample comprising the following steps:

(a) Provide a sample suspected to contain the M gene of Influenza A subtype H1N1, H3N2, H5N1, or H7N9, and/or the NS gene of Influenza B virus;

(b) provide a pair of primers comprising a forward and a reverse primer specific to the M gene of Influenza A subtype H1N1, H3N2, H5N1, and H7N9, wherein the forward primer is selected from a group of SEQ ID NO:2, SEQ ID NO:3, SEQ ID NO:4, SEQ ID NO:5, SEQ ID NO:6, SEQ ID NO:7, and SEQ ID NO:8; and the reverse primer is selected from a group of SEQ ID NO:11, SEQ ID NO:12, SEQ ID NO:13, SEQ ID NO:14, SEQ ID NO:15, SEQ ID NO:16, SEQ ID:17 NO, and SEQ ID NO:18;

(c) provide a pair of primers comprising a forward and a reverse primer specific to the NB gene of Influenza B virus, wherein the forward primer is selected from a group of SEQ ID NO:20, SEQ ID NO:21, SEQ ID NO:22, SEQ ID NO:23, SEQ ID NO:24, and SEQ ID NO:25; and the reverse primer is selected from a group of SEQ ID NO:29, SEQ ID NO:30, SEQ ID NO:31, SEQ ID NO:32, SEQ ID NO:33, SEQ ID NO:34, SEQ ID NO:35, and SEQ ID NO:36;

(d) amplify the nucleic acids contained in the suspected sample with a reverse transcriptase and a template-dependent polymerase;

(e) anneal two different probes to the nucleic acids contained in the suspected sample to form a hybridized product during step (d), wherein the first probe specific to the Influenza A subtypes H1N1, H3N2, H5N1, and H7N9 is selected from a group of SEQ ID NO:9 and SEQ ID NO:10; and the second probe specific to the Influenza B virus is selected from a group of SEQ ID NO:27 and SEQ ID NO:28; and (f) detect two distinct signals generated from the RT-PCR products as an indicator of the presence of the target nucleic acid of the Influenza A subtypes H1N1, H3N2, H5N1, and H7N9 and/or Influenza B virus, respectively.

According to the present invention, the signals generated from the hybridized products can be detected by a fluorescent detection system. One of the two distinct signals specific to the first probe is the indication of the presence of Influenza A subtypes H1N1, N3N2, H5N1, and/or H7N9, and the other specific to the second probe is the indication of the presence of the Influenza B virus.

This SUMMARY is provided to briefly identify some aspects of the present invention that are further described below in the DETAILED DESCRIPTION. This SUMMARY is not intended to identify key or essential features of the present disclosure nor is it intended to limit the scope of any claims. The term "aspects" is to be read as "at least one aspect." The aspects described above and other aspects of the present disclosure described herein are illustrated by way of example(s) and not limited in the accompanying drawing.

DETAILED DESCRIPTION OF THE INVENTION

Figure 1:
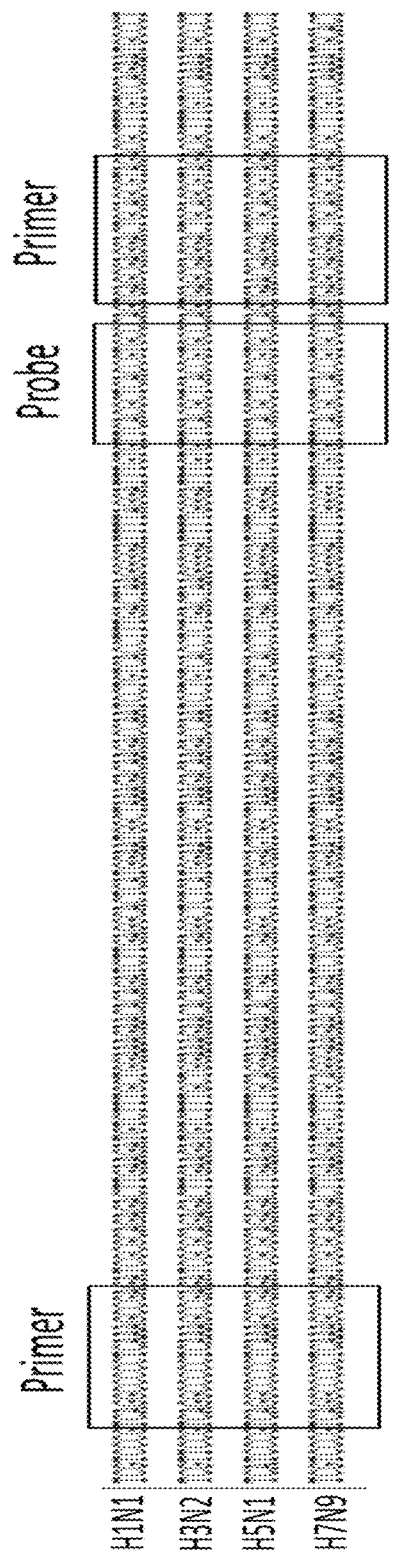
FIG. 1 illustrates the M gene primer sequence region of 4 Influenza A subtypes.

The following merely illustrates the principles of the invention. It will thus be appreciated that those skilled in the art will be able to devise various arrangements which, although not explicitly described or shown herein, embody the principles of the invention and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements later developed that perform the same function, regardless of structure.

Unless otherwise explicitly specified herein, the drawings are not drawn to scale.

To make sure the method can be processed successfully, the present invention provides a PCR or real-time PCR assay for rapid identification using TaqMan probes with conjugated minor groove binder (MGB) ligands.

In such assays, labeling the type-specific probes with different fluorescent reporters has ensured the detection of type-specific fluorescence. The Taq polymerase applied in this assay is a DNA-dependent polymerase with exonuclease hydrolysis function. The fluorescent signals are detected by the quantity of the fragments of the fluorescent reporter, which are cleaved from the probe hybridized to the target nucleic acid by an exonuclease hydrolysis of the DNA-dependent polymerase. The primer and/or probe comprise(s) a modified nucleotide or a non-nucleotide compound.

Currently, H1N1 and H3N2 are two commonly seen Influenza A subtypes leading to global pandemic infections circulating in humans. On the other hand, though H5N1 and H7N9 are uncommon Influenza A subtypes, they are very likely to cause severe disease and lead to high mortality rates in humans. Therefore, it is important to detect these four Influenza A subtypes as early as possible so that treatment can be initiated early. Also, since these four subtypes are all important, there is no need to discriminate any one of them from the others in the suspected samples. The present invention discloses a method for detecting a specific sequence shared and present in all four Influenza A subtypes H1N1, H3N2, H5N1 and H7N9. If the detection result of the present invention is positive for a suspected sample, that means at least one subtype is present. Then early treatment can begin.

The M gene (SEQ ID NO: 1) exists in Influenza A subtypes H1N1, H3N2, H5N1 and H7N9, and translates into the matrix protein (hereinafter "M protein") that lies beneath the viral envelope in the form of dimers and interacts with viral ribonucleoprotein (vRNP) complex, forming a bridge between the inner core components and the membrane proteins. vRNPs harbor the determinants for host range. The M protein contacts with both viral RNA and vRNP, promoting the formation of RNP complexes and causing the dissociation of RNP from the nuclear matrix. The M gene plays a vital role in assembly by recruiting the viral components to the site of assembly and essential role in the budding process including formation of viral particles. Novel vaccines targeting M proteins to confer cross-subtype protection have been shown to be promising.

Therefore, given that the M gene exists in Influenza A subtypes H1N1 (SEQ ID NO:47), H3N2 (SEQ ID NO:48), H5N1 (SEQ ID NO:49) and H7N9 (SEQ ID NO:50), all primers and probes disclosed in the present invention are selected from and specific to the M gene of all four subtypes as shown in FIG. 1. To be more precise, the forward primer for detection of Influenza A subtypes H1N1, H3N2, H5N1 and H7N9 is selected from the group of SEQ ID NO:2, SEQ ID NO:3, SEQ ID NO:4, SEQ ID NO:5, SEQ ID NO:6, SEQ ID NO:7, and SEQ ID NO:8; and the reverse primer is selected from the group of SEQ ID NO:11, SEQ ID NO:12, SEQ ID NO:13, SEQ ID NO:14, SEQ ID NO:15, SEQ ID NO:16, SEQ ID NO:17, and SEQ ID NO:18. The probe, which is one of the group of SEQ ID NO: 9 and SEQ ID NO:10, is also specific to the M gene. The presence of the fluorescence signal is indicative of Influenza A subtypes H1N1, H3N2, H5N1 or H7N9 in a sample.

The NS gene exists in both Influenza A virus and Influenza B virus which express the NS protein during the replication stage. However, unique biological activities of the NS gene of Influenza B virus are indicated by its deficiency to inhibit pre-mRNA processing and by <20% sequence identity to the NS gene of Influenza A virus. The NS protein is a homo-dimeric RNA-binding protein found in Influenza B virus, which is a necessary factor for viral replication. During the replication stage, the NS protein binds poly-A tails of mRNA for keeping them in the nucleus. Given that the NS gene of Influenza B virus (SEQ ID NO: 19) is highly conserved in both Influenza B/Yamagata/16/88-like and B/Victoria/2/87-like viruses, the primer and probe sequences specific to Influenza B virus disclosed in the present invention are selected from NS gene.

The internal control used in the present invention includes, but is not limited to, RNA oligonucleotide (e.g. Alere™ i Influenza A & B 2 Test, Abbott, Abbott Park, Ill. 60064, U.S.A.), encapsulated (armored) RNA pseudovirus (e.g. Xpert® Flu/RSV XC Assay, Cepheid, Sunnyvale, Calif. 94089, U.S.A.), encapsulated RNA (e.g. cobas® Liat® Influenza A/B & RSV, Roche, Basel, Switerland), in vitro transcribed RNA (e.g. ProFlu+™ Assay Test), armored RNA (e.g. Simplexa™ Influenza A H1N1 (2009) Kit, Focus Diagnostics), encapsulated RNA (e.g. Simplexa™ Flu A/B & RSV Direct Kit, Focus Diagnostics), mengovirus (e.g. encephalomyocarditis virus (EMCV) RT-PCR kit), bacteriophage (e.g. Adenovirus R-GENE®, adenovirus species (A, B, C, D, E, F and G)), noninfectious armored RNA (e.g. in vitro PCR based assay for HCV RNA detection), bacteriophage MS2 (e.g. RIDA® GENE Norovirus GI/GII, Clinical Diagnostics), tobacco mosaic virus (TMV), phocine distemper virus, brome mosaic virus (BMV), and so on. Ms2, an ssRNA bacteriophage, is commonly used as an internal control in biological experiments and virus/pathogen detections after a preliminary reverse transcription process. The application of internal control is included for monitoring the adequate processing of the target viruses and the presence of inhibition factors in the RT-PCR reactions to prevent false-negative results due to inhibition or human error. Therefore, in the following embodiments, ms2 is added as an internal control into the detection tube containing the Influenza A subtypes H1N1, H3N2, H5N1, H7N9, and/or Influenza B virus to be detected. The full length complementary DNA of ms2 generated from reverse transcription is as represented by SEQ ID NO:37.

The present invention using TaqMan probes is more sensitive than a traditional method, where the limit of detection (hereinafter LOD) of the present invention can reach $10^1$ copies on Influenza A subtypes H1N1, H3N2, H5N1 or H7N9, as well as on Influenza B virus. Therefore, the present invention is suitable for rapid and unambiguous detection of Influenza A subtypes H1N1, H3N2, H5N1, and H7N9 and Influenza B virus.

In one embodiment of the present invention, a serial step(s) are provided for testing the LOD of Influenza A subtypes H1N1, H3N2, H5N1, and H7N9 and Influenza B virus in a known-concentration (virus particle copy number) sample comprising the following steps:

(a) Prepare two serial single dilutions of at least one subtype of Influenza A subtype H1N1, H3N2, H5N1, or H7N9 from $10^3$ virus copy number to $10^2$ and $10^1$, wherein these three serial dilutions contain the M gene of Influenza A subtypes H1N1, H3N2, H5N1, or H7N9;

(b) prepare two serial single dilutions of at least one subtype of Influenza B virus from $10^3$ virus copy number to $10^2$ and $10^1$, wherein these three serial dilutions contain the NS gene of Influenza B virus;

(c) provide a pair of primers comprising a forward and a reverse primer specific to the M gene of Influenza A subtype H1N1, H3N2, H5N1, and H7N9, wherein the forward primer is selected from a group of SEQ ID NO:2, SEQ ID NO:3, SEQ ID NO:4, SEQ ID NO:5, SEQ ID NO:6, SEQ ID NO:7, and SEQ ID NO:8; and the reverse primer is selected from a group of SEQ ID NO:11, SEQ ID NO:12, SEQ ID NO:13, SEQ ID NO:14, SEQ ID NO:15, SEQ ID NO:16, SEQ ID NO:17, and SEQ ID NO:18;

(d) provide a pair of primers comprising a forward and a reverse primer specific to the NS gene of Influenza B virus, wherein the forward primer is selected from a group of SEQ ID NO:20, SEQ ID NO:21, SEQ ID NO:22, SEQ ID NO:23, SEQ ID NO:24, and SEQ ID NO:25; and the reverse primer is selected from a group of SEQ ID NO:29, SEQ ID NO:30, SEQ ID NO:31, SEQ ID NO:32, SEQ ID NO:33, SEQ ID NO:34, SEQ ID NO:35, and SEQ ID NO:36;

(e) add the ms2 into all serial dilutions of Influenza A virus and Influenza B virus, and then add a pair of primers comprising a forward and a reverse primer of the ms2 as an internal control into all serial dilutions, wherein the forward primer is selected from a group of SEQ ID NO:38, SEQ ID NO:39, SEQ ID NO:40, and SEQ ID NO:41; and the reverse primer is selected from a group of SEQ ID NO:43, SEQ ID NO:44, SEQ ID NO:45, and SEQ ID NO:46;
(f) amplify the nucleic acids contained in the known-concentration samples of Influenza A virus, Influenza B virus and the internal control with a reverse transcriptase and a template-dependent polymerase;
(g) anneal two different probes to the nucleic acids contained in the known-concentration samples to form a hybridized product during step (f), wherein the first probe specific to the Influenza A subtypes H1N1, H3N2, H5N1, and H7N9 is selected from a group of SEQ ID NO:9 and SEQ ID NO:10; and the second probe specific to the Influenza B virus is selected from a group of SEQ ID NO:27 and SEQ ID NO:28;
(h) anneal the probe specific to the ms2 to form a hybridized product during step (f), wherein the probe sequence is as SEQ ID NO:42; and
(i) To detect three distinct signals generated from the hybridized products as an indicator of the presence of the target nucleic acid of the Influenza A subtypes H1N1, H3N2, H5N1, and H7N9 and/or Influenza B virus and the internal control, respectively.

In another embodiment of the present invention, a method is provided for the detection of the presence of at least one of Influenza A subtype H1N1, H3N2, H5N1, and H7N9, and/or Influenza B virus in one suspected sample comprising the following steps:
(a) Provide a sample suspected to contain the M gene of Influenza A subtypes H1N1, H3N2, H5N1, and H7N9, and/or the NS gene of Influenza B virus;
(b) provide a pair of primers comprising a forward and a reverse primer specific to the M gene of Influenza A subtypes H1N1, H3N2, H5N1, and H7N9, wherein the forward primer is selected from a group of SEQ ID NO:2, SEQ ID NO:3, SEQ ID NO:4, SEQ ID NO:5, SEQ ID NO:6, SEQ ID NO:7, and SEQ ID NO:8; and the reverse primer is selected from a group of SEQ ID NO:11, SEQ ID NO:12, SEQ ID NO:13, SEQ ID NO:14, SEQ ID NO:15, SEQ ID NO:16, SEQ ID NO:17, and SEQ ID NO:18;
(c) provide a pair of primers comprising a forward and a reverse primer specific to the NS gene of Influenza B virus, wherein the forward primer is selected from a group of SEQ ID NO:20, SEQ ID NO:21, SEQ ID NO:22, SEQ ID NO:23, SEQ ID NO:24, and SEQ ID NO:25; and the reverse primer is selected from a group of SEQ ID NO:29, SEQ ID NO:30, SEQ ID NO:31, SEQ ID NO:32, SEQ ID NO:33, SEQ ID NO:34, SEQ ID NO:35, and SEQ ID NO:36;
(d) provide the ms2 and a pair of primers comprising a forward and a reverse primer of the ms2 as an internal control, wherein the forward primer is selected from a group of SEQ ID NO:38, SEQ ID NO:39, SEQ ID NO:40, and SEQ ID NO:41; and the reverse primer is selected from a group of SEQ ID NO:43, SEQ ID NO:44, SEQ ID NO:45, and SEQ ID NO:46;
(e) amplify the nucleic acids contained in the suspected sample and the internal control with a reverse transcriptase and a template-dependent polymerase;
(f) anneal two different probes to the nucleic acids contained in the suspected sample to form a hybridized product during step (e), wherein the first probe specific to the Influenza A subtypes H1N1, H3N2, H5N1, and H7N9 is selected from a group of SEQ ID NO:9 and SEQ ID NO:10; and the second probe specific to the Influenza B virus is selected from a group of SEQ ID NO:27 and SEQ ID NO:28;
(g) anneal the probe specific to the ms2 to form a hybridized product during step (e), wherein the probe sequence is as SEQ ID NO:42; and
(h) detect three distinct signals generating from the hybridized products as an indicator of the presence of the target nucleic acid of the Influenza A subtypes H1N1, H3N2, H5N1, and H7N9 and/or Influenza B virus and the internal control, respectively.

Embodiment 1 LOD of Influenza A Subtypes H1N1, H3N2, H5N1, and H7N9

H3N2 particles of known-concentration were used in this embodiment as the representative of Influenza A subtypes H1N1, H3N2, H5N1, and H7N9. Two serial dilutions were prepared from $10^3$ copy number to $10^2$ and $10^1$ copy number. Primers having SEQ ID NO:5 (F) and SEQ ID NO:18 (R) are used to amplify the M gene of Influenza A subtypes H1N1, H3N2, H5N1, or H7N9. A probe having SEQ ID NO: 9 is also used in this embodiment. The probe can also be replaced with SEQ ID NO: 10. For internal control, primers having SEQ ID NO: 39 (F) and SEQ ID NO:45 (R) are used to amplify the ms2. A probe having SEQ ID NO: 42 is also used in this embodiment. The primer and probe sequences are shown in Table 1.

TABLE 1

Primer Sequence
Primers used in the examples

| Sequence ID | Function | Sequence 5'-3' |
|---|---|---|
| M gene | | |
| SEQ ID NO: 5 | Forward primer | TCAGGCCCCCTCAAAGCCGA |
| SEQ ID NO: 18 | Reverse primer | CTACGCTGCAGTCCTCGCTCA |
| SEQ ID NO: 9 | probe | TTCACGCTCACCGTGCC |
| ms2 | | |
| SEQ ID NO: 39 | Forward primer | CTGGCGCGTACGTAAAGTCTCC |
| SEQ ID NO: 45 | Reverse primer | GACCCCGTTAGCGAAGTTGC |
| SEQ ID NO: 42 | probe | CCCTCAACCGGAGTTTGAAGCATG |

The amplification was carried out and was measured and monitored in real-time on a Roche Light Cycler 96 Real-time System (Roche Molecular Systems, Inc.). Each reaction mixture volume was 20 μl, and was amplified under the following conditions:

TABLE 2

Conditions of the Amplification of the reference samples

| | H3N2 particles | | | Negative |
|---|---|---|---|---|
| | $10^3$ | $10^2$ | $10^1$ | control |
| Sample RNA template | | 1 μl | | 0 |
| Flu A Primer (F) | | 0.3 μM | | |

TABLE 2-continued

Conditions of the Amplification of the reference samples

| | H3N2 particles | | | Negative control |
|---|---|---|---|---|
| | $10^3$ | $10^2$ | $10^1$ | |
| Flu A Primer (R) | | 0.3 μM | | |
| Flu A Probe | | 0.15 μM | | |
| ms2 | | $10^2$ copies | | |
| ms2 primer (F) | | 0.3 μM | | |
| ms2 primer (R) | | 0.3 μM | | |
| ms2 probe | | 0.15 μM | | |
| dNTP | | 0.5 mM | | |
| DNA Polymerase | | 5 units | | |
| RNA dependent DNA polymerase | | 20 units | | |
| RNase inhibitor | | 10 units | | |
| Total Volume | | 20 μl | | |

The reaction mixtures were firstly subjected to reverse transcription for 2 minutes at 50° C. The actual amplification reaction was first incubated at 95° C. for 2 min, and then carried out for 50 cycles according to the following scheme:

95° C. 1 sec.→60° C. 1 sec.

Figure 2:
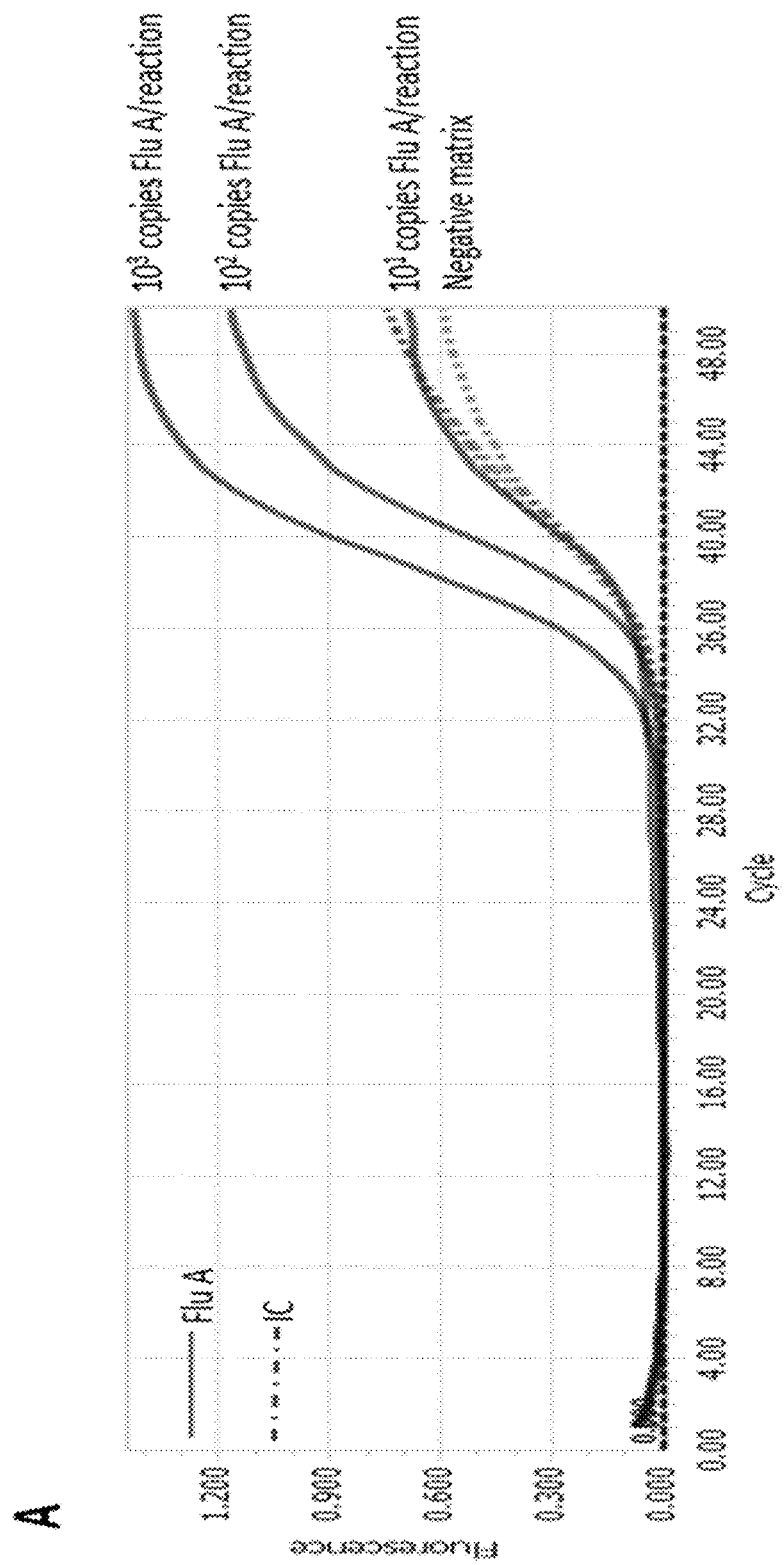
FIG. 2 illustrates the kinetic PCR growth curves of embodiment 1.

FIG. 2 shows the kinetic PCR growth curve for the given pair of primers, probes, and internal control. When the growth curves of the $10^3$, $10^2$, and $10^1$ of H3N2 particles exceed the threshold, an unambiguous and specific signal is initially detectable. The detection limit could reach to $10^1$ copy number under such condition and primer sequences.

In other words, if a suspected sample was infected by Influenza A subtypes H1N1, H3N2, H5N1, or H7N9, all of which contain the M gene sequence, a climbing curve will show in the kinetic PCR growth curve. In the meantime, the ms2 signal is also detectable as a representative of adequate process.

Embodiment 2 LOD of Influenza B Virus

The Malaysia 2506/2004 strain, which is a strain of Influenza B/Victoria/2/87-like virus, was used in this embodiment as the representative of two lineages of Influenza B virus. Two serial dilutions were prepared from $10^3$ virus copy number to $10^2$ and $10^1$ copy number. Primers having SEQ ID NO:22 (F) and SEQ ID NO:33 (R) are used to amplify a suspected NS gene of Influenza B virus. A probe having SEQ ID NO: 28 is also used in this embodiment. The probe can also be replaced to SEQ ID No: 27. For internal control, primers having SEQ ID NO: 39 (F) and SEQ ID NO:45 (R) are used to amplify the ms2. A probe having SEQ ID NO: 42 is also used in this embodiment. The primer and probe sequences are shown in Table 3.

TABLE 3

Primer Sequence
Primers used in the examples

| Sequence ID | Function | Sequence 5'-3' |
|---|---|---|
| | NS gene | |
| SEQ ID NO: 22 | Forward primer | AAGATGGCCATCGGATCCTC |
| SEQ ID NO: 33 | Reverse primer | GGTGATAATCGGTGCTCTTGACC |
| SEQ ID NO: 28 | probe | CCAATTCGAGCAGCTGAAACTGCG |
| | ms2 | |
| SEQ ID NO: 39 | Forward primer | CTGGCGCGTACGTAAAGTCTCC |
| SEQ ID NO: 45 | Reverse primer | GACCCCGTTAGCGAAGTTGC |
| SEQ ID NO: 42 | probe | CCCTCAACCGGAGTTTGAAGCATG |

The amplification was carried out and was measured and monitored in real-time on a Roche Light Cycler 96 Real-time System (Roche Molecular Systems, Inc.). Each reaction mixture volume was 20 μl, and was amplified under the following conditions:

TABLE 4

Conditions of the Amplification of the reference samples

| | Influenza B virus particles | | | Negative control |
|---|---|---|---|---|
| | $10^3$ | $10^2$ | $10^1$ | |
| Sample RNA template | 1 μl | | | 0 |
| Flu B Primer (F) | | 0.3 μM | | |
| Flu B Primer (R) | | 0.3 μM | | |
| Flu B Probe | | 0.15 μM | | |
| ms2 | | $10^2$ copies | | |
| ms2 primer (F) | | 0.3 μM | | |
| ms2 primer (R) | | 0.3 μM | | |
| ms2 probe | | 0.15 μM | | |
| dNTP | | 0.5 mM | | |
| DNA Polymerase | | 5 unit | | |
| RNA dependent DNA polymerase | | 20 unit | | |
| RNase inhibitor | | 10 unit | | |
| Total Volume | | 20 μl | | |

The reaction mixtures were firstly subjected to reverse transcription for 2 minutes at 50° C. The actual amplification reaction was first incubated at 95° C. for 2 min, and then carried out for 50 cycles according to the following scheme:

95° C. 1 sec.→60° C. 1 sec.

Figure 3:
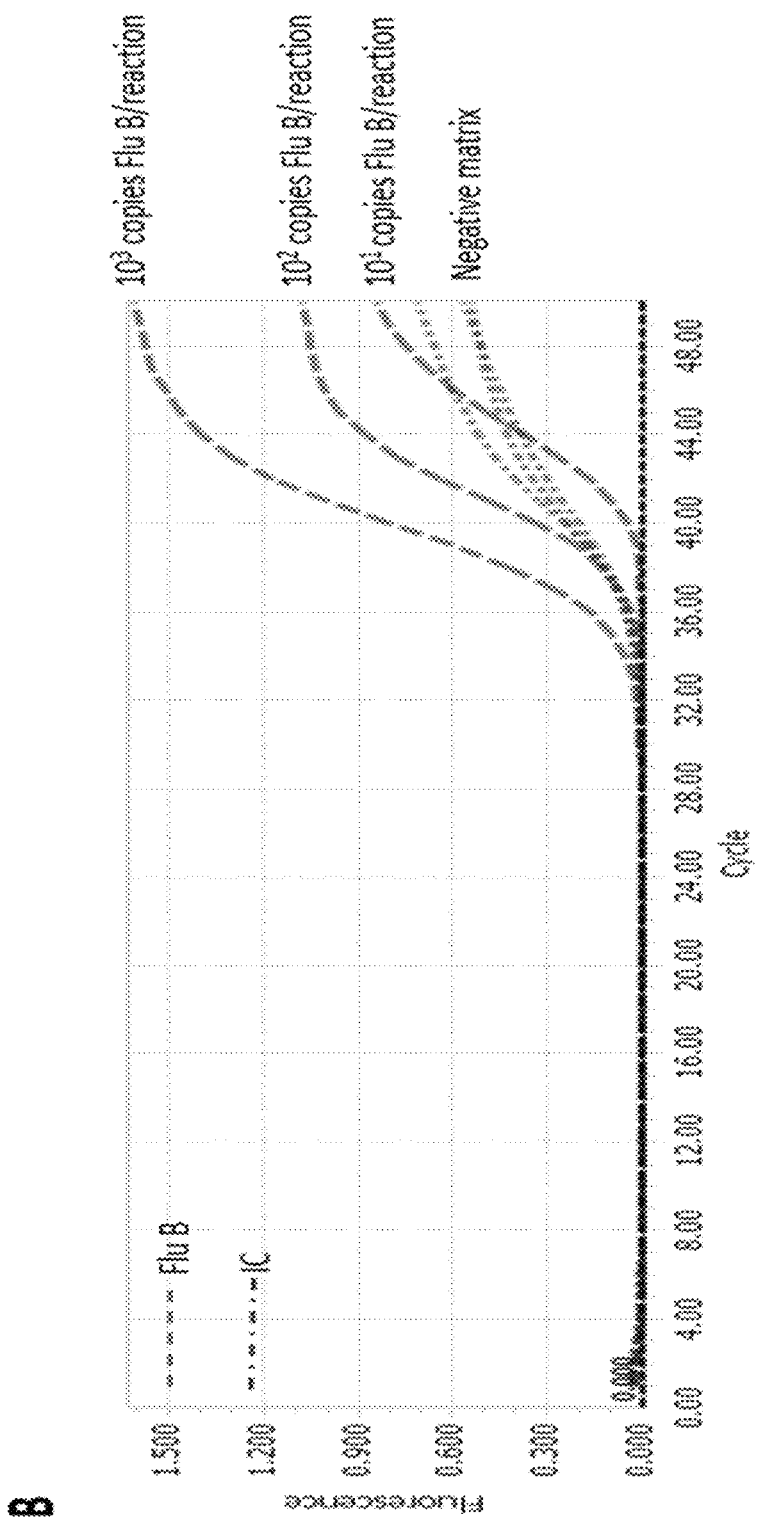
FIG. 3 illustrates the kinetic PCR growth curves of embodiment 2.

FIG. 3 shows the kinetic PCR growth curve for the given pair of primers, probes, and internal control. When the growth curves of the $10^3$, $10^2$, and $10^1$ of Malaysia 2506/2004 particles exceed the threshold, an unambiguous and specific signal is initially detectable. The detection limit could reach to $10^1$ copy number in this condition.

In other words, if a suspected sample was infected by Influenza B virus, which contains the NS gene sequence, a climbing curve will show in the kinetic PCR growth curve. In the meantime, the ms2 signal is also detectable as a representative of adequate process.

Embodiment 3 Influenza A Subtypes H1N1, H3N2, H5N1, and H7N9 and Influenza B Virus Detection The present invention discloses a method to detect the presence of at least one of the four Influenza A subtypes H1N1, H3N2, H5N1, and H7N9, and/or Influenza B virus, respectively. Preferably, the present invention does not comprise the step of sample preparation. After purification or isolation of the nucleic acids from a suspected sample, which might be throat/nasal swabs or nasopharyngeal swabs, the nucleic acids are contained in the sample collection buffer.

This embodiment is to provide a detection method for detecting the presence of the M gene of Influenza A subtypes H1N1, H3N2, H5N1, or H7N9 in a suspected sample of an unknown patient with flu-like symptoms, wherein the nucleic acid of the suspected samples is contained in the sample collection buffer as mentioned above. The presence of the NS gene of Influenza B virus is also detected simultaneously. To be more precise, if a suspected sample contains at least one of Influenza A subtype H1N1, H3N2, H5N1, or H7N9, the detection result would reflect such outcome that at least one subtype of Influenza A virus is present in this suspected sample regardless of which one of these four subtypes is present. Also, if a suspected sample contains at least one strain of Influenza B virus, it would also be detected by this invention simultaneously. And also, if a suspected sample contains at least one of Influenza A subtype H1N1, H3N2, H5N1 and H7N9 and/or Influenza B virus, then it would be detected separately.

For detecting at least one of Influenza A subtypes H1N1, H3N2, H5N1, or H7N9, primers having SEQ ID NO:5 (F) and SEQ ID NO:18 (R) are used to amplify the M gene of Influenza A subtypes H1N1, H3N2, H5N1, or H7N9. A probe having SEQ ID NO: 9 is also used in this embodiment. For internal control, primers having SEQ ID NO: 39 (F) and SEQ ID NO:45 (R) are used to amplify the ms2. A probe having SEQ ID NO: 42 is also used in this embodiment. The primer and probe sequences are shown in Table 1.

For detecting Influenza B virus, primers having SEQ ID NO:22 (F) and SEQ ID NO:33 (R) are used to amplify a suspected NS gene of Influenza B virus. A probe having SEQ ID NO: 28 is also used in this embodiment. For internal control, primers having SEQ ID NO: 39 (F) and SEQ ID NO:45 (R) are used to amplify the ms2. A probe having SEQ ID NO: 42 is also used in this embodiment. The primer and probe sequences are shown in Table 3.

The amplification was carried out and was measured and monitored in real-time on a Roche Light Cycler 96 Real-time System (Roche Molecular Systems, Inc.). Each reaction mixture volume was 20 µl, and was amplified under the following conditions:

TABLE 5

Conditions of the Amplification of the reference samples

| | Samples to-be detected | Negative control |
|---|---|---|
| Sample RNA template | 1 µl | 0 |
| Flu A Primer (F) | 0.3 µM | |
| Flu A Primer (R) | 0.3 µM | |
| Flu B Primer (F) | 0.3 µM | |
| Flu B Primer (R) | 0.3 µM | |
| Flu A Probe | 0.15 µM | |
| Flu B Probe | 0.15 µM | |
| ms2 | $10^2$ copies | |
| ms2 primer (F) | 0.3 µM | |
| ms2 primer (R) | 0.3 µM | |
| ms2 probe | 0.15 µM | |
| dNTP | 0.5 mM | |
| DNA Polymerase | 5 units | |
| RNA dependent DNA polymerase | 20 units | |
| RNase inhibitor | 10 units | |
| Total Volume | 20 µl | |

The reaction mixtures were firstly subjected to reverse transcription for 2 minutes at 50° C. The actual amplification reaction was first incubated at 95° C. for 2 min, and then carried out for 50 cycles according to the following scheme:

95° C. 1 sec.→60° C. 1 sec.

Figure 4:
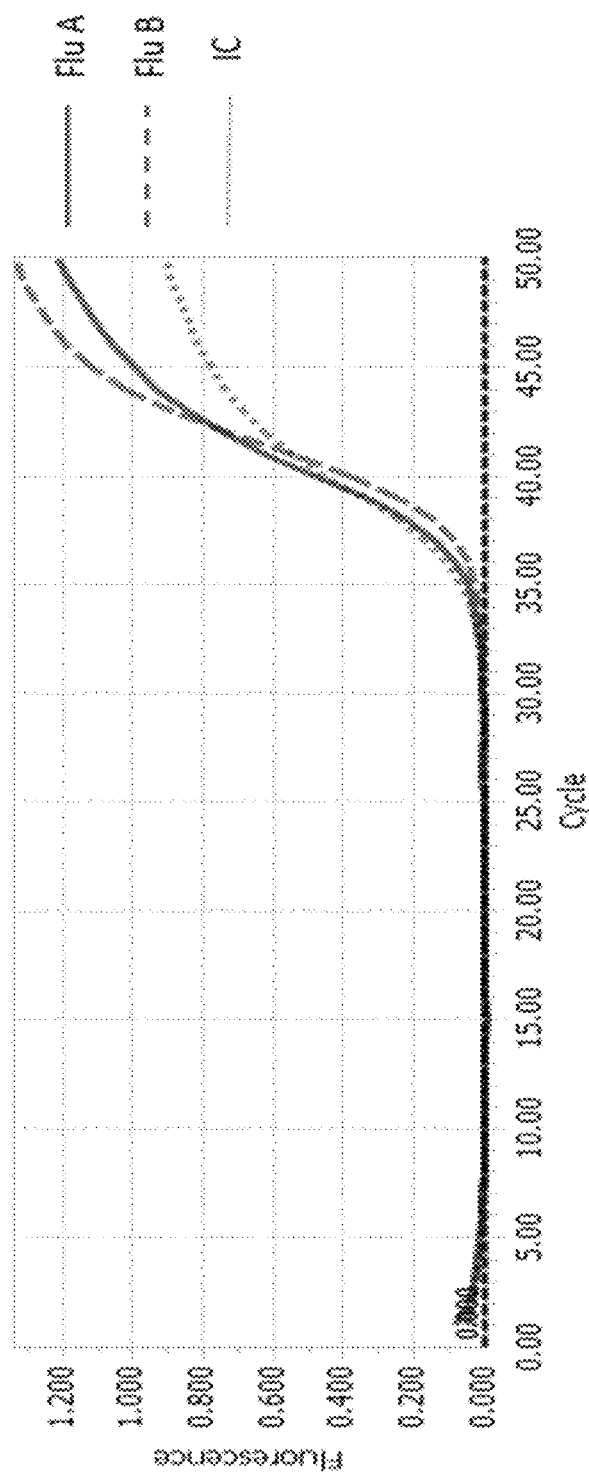
FIG. 4 illustrates the kinetic PCR growth curves of embodiment 3.

FIG. 4 shows the kinetic PCR growth curve for the given pair of primers, probes, and internal control. In FIG. 4, the detection results show that the suspected sample contained at least one of Influenza A subtype H1N1, H3N2, H5N2, and H7N9, and Influenza B virus. The suspected sample was then processed with a sequencing procedure, and the results showed that the suspected sample contained Influenza A H3N2 and Influenza B virus Malaysia 2506/2004.

Embodiment 4 Random Detection of Influenza A Subtypes H1N1, H3N2, H5N1, and H7N9 and Influenza B Virus In this embodiment, a test for the detection specificity of the present invention is provided. The specificity of a clinical detection refers to the ability of the detection to correctly identify those samples without the disease/symptom. Therefore, a detection with 100% specificity correctly identifies all samples without the disease/symptom. A detection with 80% specificity correctly reports 80% of samples without the disease/symptom as detection negative (true negatives) but 20% samples without the disease/symptom are incorrectly identified as detection positive (false positives). In order to test the specificity of the present invention, 4 samples not belonging to the Orthomyxoviridae species as listed below are provided in this embodiment. The TCID50 of each species is higher than $1.43*10^5$/ml.

TABLE 6

Sample list of the 4 samples

| No. 1 | Parainfluenza virus type 1 |
|---|---|
| No. 2 | Parainfluenza virus type 2 |
| No. 3 | Parainfluenza virus type 3 |
| No. 4 | Human coxsackievirus A16 |

The same preparation procedures and amplification conditions are used in these 4 samples, including the designated primers and probes which are specific to Influenza A H1N1, H3N2, H5N1, and H7N9 (Primers: SEQ ID NO:5 and SEQ ID NO:18; Probe: SEQ ID NO: 9), and Influenza B virus (Primers: SEQ ID NO:22 and SEQ ID NO:33; Probe: SEQ ID NO: 28), respectively. The ms2 particles, the primers, and the probe (Primers: SEQ ID NO: 39 and SEQ ID NO:45; Probe: SEQ ID NO: 42) are also used in this embodiment as an internal control.

The amplification is carried out and was measured and monitored in real-time on a Roche Light Cycler 96 Real-time System. (Roche Molecular Systems, Inc.) Each reaction mixture volume was 20 µl, and was amplified under the following conditions:

TABLE 7

Conditions of the Amplification of the reference samples

| | Samples to-be detected | Negative control |
|---|---|---|
| Suspected Sample | 1 µl | 0 |
| Flu A Primer (F) | 0.3 µM | |
| Flu A Primer (R) | 0.3 µM | |
| Flu B Primer (F) | 0.3 µM | |
| Flu B Primer (R) | 0.3 µM | |

TABLE 7-continued

Conditions of the Amplification of the reference samples

| | Samples to-be detected | Negative control |
|---|---|---|
| Flu A Probe | 0.15 μM | |
| Flu B Probe | 0.15 μM | |
| ms2 | $10^2$ copies | |
| ms2 primer (F) | 0.3 μM | |
| ms2 primer (R) | 0.3 μM | |
| ms2 probe | 0.15 μM | |
| dNTP | 0.5 mM | |
| DNA Polymerase | 5 units | |
| RNA dependent DNA polymerase | 20 units | |
| RNase inhibitor | 10 units | |
| Total Volume | 20 μl | |

The reaction mixtures were firstly subjected to reverse transcription for 2 minutes at 50° C. The actual amplification reaction was first incubated at 95° C. for 2 min, and then carried out for 50 cycles according to the following scheme:

95° C. 1 sec.→60° C. 1 sec.

Figure 5:
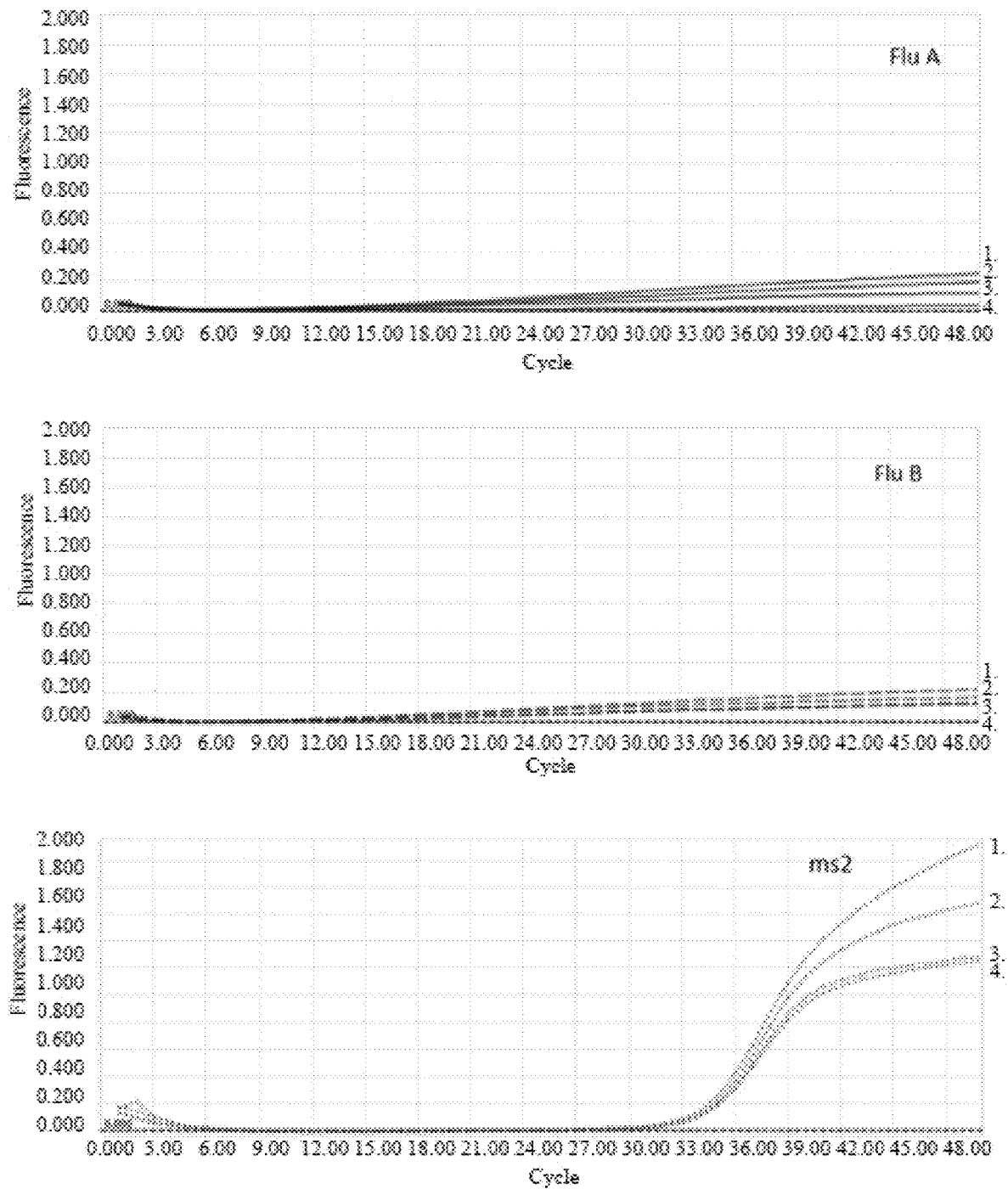
FIG. 5 illustrates the specificity test result of embodiment 4.

FIG. 5 shows the kinetic PCR growth curve for the given pair of primers, probes, and internal control. In FIG. 5, the detection results of these four samples show that no samples were detected and recognized as Influenza A subtypes H1N1, H3N2, H5N1, and H7N9, nor as Influenza B virus while the internal controls of each species were normally detected. Therefore, the specificity of the present invention is able to reach a 100% specificity correction in identifying Influenza A subtypes H1N1, H3N2, H5N1, or H7N9, as well as to the Influenza B virus.

We claim:

1. A method for detecting the presence of Influenza A subtypes H1N1, H3N2, H5N1, or H7N9, and the Influenza B virus in a suspected sample in a single container, comprising the steps of:
   (a) providing a sample suspected to contain the matrix gene of Influenza A subtypes H1N1, H3N2, H5N1, or H7N9, wherein the sample is also suspected to contain the non- structural gene of Influenza B virus,
   (b) providing a pair of primers for detecting the matrix gene of Influenza A virus comprising a first primer and a second primer, wherein the first primer is selected from the group consisting of SEQ ID NO:2, SEQ ID NO:3, SEQ ID NO:4, SEQ ID NO:5, SEQ ID NO:6, SEQ ID NO:7, SEQ ID NO:8, and SEQ ID NO:14, and wherein the second primer is selected from the group consisting of SEQ ID NO:11, SEQ ID NO:12, SEQ ID NO:13, SEQ ID NO: 15, SEQ ID NO: 16, and SEQ ID NO: 18, (c) providing a pair of primers for detecting the non-structural gene of Influenza B virus comprising a third primer and a fourth primer, wherein the third primer is selected from the group consisting of SEQ ID NO:20, SEQ ID NO:21, SEQ ID NO:22, SEQ ID NO:23, SEQ ID NO:24, SEQ ID NO:25, and SEQ ID NO:26, and wherein the fourth primer is selected from the group consisting of SEQ ID NO:29, SEQ ID NO:30, SEQ ID NO:31, SEQ ID NO:32, SEQ ID NO:33, SEQ ID NO:34, SEQ ID NO:35, and SEQ ID NO:36, (d) providing a pair of primers comprising a forward primer and a reverse primer of an internal control, wherein the forward primer is selected from the group consisting of SEQ ID NO:38, SEQ ID NO:39, SEQ ID NO:40, and SEQ ID NO:41, and the reverse primer is selected from the group consisting of SEQ ID NO:43, SEQ ID NO:44, SEQ ID NO:45, and SEQ ID NO:46, (e) disposing the sample, the first, the second, the third and the fourth primers, the forward and the reverse primers of the internal control, a first, a second and a third probe, and the internal control in the single container and amplifying a target nucleic acid with a reverse transcriptase and a template-dependent polymerase, (f) annealing the first and the second probes to the target nucleic acid to form a first hybridized product and a second hybridized product during step (e), wherein the first probe is specific to the matrix gene of Influenza A virus and the sequence of the first probe is selected from the group consisting of SEQ ID NO:9 and SEQ ID NO: 10, and the second probe is specific to the non-structural gene of Influenza B virus and is selected from the group consisting of SEQ ID NO:27 and SEQ ID NO:28, (g) annealing the third probe to the target nucleic acid to form a third hybridized product during step (e), wherein the third probe is specific to the internal control and the sequence of the third probe is SEQ ID NO:42, and (h) detecting signals generated from the first, the second and the third hybridized products as an indicator of the presence of the target nucleic acid.

2. The method according to claim 1, wherein the signals generated from the first, the second and the third hybridized products are fluorescent signals.

3. The method according to claim 2, wherein all 5'-terminals of the first, the second, and the third probes carry fluorescent reporters, which are selected from the group consisting of FAM, HEX, VIC, CY3, CY5, TFT, ALEXA594, and ALEXA643; and the 3'-terminals of the three probes carry quenchers, which are selected from the group consisting of TAMRA, MGB, and BHQ; and wherein the fluorescent reporters of all of the three probes are distinct.

4. The method according to claim 3, wherein the three distinct fluorescent signals generated from the three hybridized products are detected by the quantity of the fragments of the fluorescent reporters, which are cleaved from the first, the second, or the third probe hybridized to the target nucleic acid by an exonuclease hydrolysis of the DNA-dependent polymerase, respectively.

5. The method according to claim 4, wherein the presence of the first fluorescent signal is indicative of the presence of the Influenza A subtypes H1N1, H3N2, H5N1, or H7N9 in the suspected sample, and wherein the absence of the first fluorescent signal is indicative of the absence of the Influenza A subtypes H1N1, H3N2, H5N1, or H7N9 in the suspected sample.

6. The method according to claim 4, wherein the presence of the second fluorescent signal is indicative of the presence of the Influenza B virus in the suspected sample, and wherein the absence of the second fluorescent signal is indicative of the absence the Influenza B virus in the suspected sample.

7. The method according to claim 1, wherein the internal control is selected from the group consisting of RNA oligonucleotide, encapsulated (armored) RNA pseudovirus, encapsulated RNA, in vitro transcribed RNA, armored RNA, encapsulated RNA, mengovirus, bacteriophage, non-infectious armored RNA, bacteriophage ms2, tobacco mosaic virus (TMV), phocine distemper virus and brome mosaic virus (BMV).

* * * * *

SEQUENCE LISTING

<160> NUMBER OF SEQ ID NOS: 50

<210> SEQ ID NO 1
<211> LENGTH: 984
<212> TYPE: DNA
<213> ORGANISM: Influenza A virus

<400> SEQUENCE: 1

```
agatgagtct tctaaccgag gtcgaaacgt acgttctctc tatcgtcccg tcaggccccc      60
tcaaagccga gatcgcacag agacttgaag atgtctttgc tgggaagaac accgatcttg     120
aggctctcat ggaatggcta aagacaagac caatcctgtc acctctgact aaggggattt     180
taggatttgt gttcacgctc accgtgccca gtgagcgagg actgcagcgt agacgctttg     240
tccaaaatgc ccttaatggg aatggggatc caaataacat ggacagagca gttaaactgt     300
atagaaagct taagagggag ataacattcc atggggccaa agaaatagca ctcagttatt     360
ctgctggtgc acttgccagt tgtatgggcc tcatatacaa caggatgggg gctgtgacca     420
ctgaagtggc atttggcctg gtatgcgcaa cctgtgaaca gattgctgac tcccagcata     480
ggtctcatag gcaaatggtg acaacaacca atccactaat aagacatgag aacagaatgg     540
ttctggccag cactacagct aaggctatgg agcaaatggc tggatcgagt gagcaagcag     600
cagaggccat ggaggttgct agtcaggcca ggcaaatggt gcaggcaatg agagccattg     660
ggactcatcc tagctccagt gctggtctga agatgatct tcttgaaaat tgcaggcct      720 atcagaaacg aatgggggtg cagatgcaac gattcaagtg atcctcttgt tgttgccgca     780
agtatcattg ggatcttgca cttgatattg tggattcttg atcgtctttt tttcaaatgc     840
atttatcgtc tctttaaaca cggtctgaaa agagggcctt ctacggaagg agtaccagag     900
tctatgaggg aagaatatcg aaaggaacag cagaatgctg tggatgctga cgatagtcat     960
tttgtcaaca tagagctgga gtaa                                           984
```

<210> SEQ ID NO 2
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 2
atgagycttc taaccgaggt cgaaacg                                         27

```
<210> SEQ ID NO 3
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 3
ctaaccgagg tcgaa                                                        15

<210> SEQ ID NO 4
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 4
cttctaaccg aggtcgaaac g                                                 21

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
tcaggccccc tcaaagccga                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
ccrtcaggcc ccctcaaagc                                                   20

<210> SEQ ID NO 7
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 7
ccctcaaagc cgagatcg                                                     18

<210> SEQ ID NO 8
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 8
atgagycttc taaccgaggt cg                                                22

<210> SEQ ID NO 9
<211> LENGTH: 17
<212> TYPE: DNA
<213> ORGANISM: Artificial Sequence
<220> FEATURE:
<223> OTHER INFORMATION: Synthetic polynucleotide
```

<400> SEQUENCE: 9
ttcacgctca ccgtgcc                                                  17

<210> SEQ ID NO 10
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 10
tttgtgttca cgctcaccgt gcc                                           23

<210> SEQ ID NO 11
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 11
cgtctacgct gcagtcctcg ctcac                                         25

<210> SEQ ID NO 12
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 12
gctgcagtcc tcgc                                                     14

<210> SEQ ID NO 13
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 13
ggtcttgtct ttagccattc catgagag                                      28

<210> SEQ ID NO 14
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 14
catggaatgg ctaaag                                                   16

<210> SEQ ID NO 15
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 15
cgctgcagtc ctcgctcac                                                19

<210> SEQ ID NO 16
<211> LENGTH: 20

<212> TYPE: DNA
<213> ORGANISM: Artificial Sequence
<220> FEATURE:
<223> OTHER INFORMATION: Synthetic polynucleotide

<400> SEQUENCE: 16
cgctgcagtc ctcgctcact            20

<210> SEQ ID NO 17
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 17
taatacgact cactataggg cgtctacgct gc            32

<210> SEQ ID NO 18
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 18
ctacgctgca gtcctcgctc a            21

<210> SEQ ID NO 19
<211> LENGTH: 1066
<212> TYPE: DNA
<213> ORGANISM: Influenza B virus

<400> SEQUENCE: 19
tgtttagtca ctggcaaaca gagaaaaatg gcgaacaaca acatgaccac aacacaaatt            60
gaggtgggtc cgggagcaac caatgccacc ataaactttg aagcaggaat tctggagtgc           120
tatgaaaggc tttcatggca agagcccttg actatcccg gtcaagaccg cctaaacaga           180
ctaaaaagaa aattagagtc aagaataaag acccacaaca aagtgagcc tgaaagtaaa           240 aggatgtccc ttgaagagag aaaagcaatt ggagtaaaaa tgatgaaagt actcctattt           300
atgaatccgt ctgctgaaat tgaagggttt gagccatact gtatgaacag ttcctcaaat           360
agcaactgta cgaaatacaa ttggaccgat taccccttcaa caccagagag gtgccttgat           420
gacatagagg aagaaccaga ggatgttgat ggcccaactg aaatagtatt aagggacatg           480
aacaacaaag atgcaaggca aagataaag gaggaagtaa acactcagaa agaagggaag           540
ttccgtttga caataaaaag ggatatacgt aatgtattgt ccttgagagt gttggtaaat           600
ggaacattcc tcaaacaccc caatggatac aagtccttgt caactctgca tagattgaat           660
gcatatgacc agagtggaag gcttgttgct aaacttgttg ccactgatga tcttacagtg           720
gaggatgaag aagatggcca tcggatcctc aactcactct tcgagcgtct caatgaagga           780
cattcaaagc caattcgagc agctgaaact gcggtgggag tcttatccca atttggtcaa           840
gagcaccgat tatcaccaga gagggagac aattagattg gtcacggaag aactttatct           900
tttaagtaaa agaattgatg ataacatact attccacaaa acgtgatag ctaacagctc           960 cataatagct gacatggttg tatcattatc attattagaa acattgtatg aaatgaagga          1020
tgtggttgaa gtgtacagca ggcagtgctt gtgaatttaa aataaa                         1066

<210> SEQ ID NO 20

```
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 20
gatgttgatg gcccaactga aatag                                            25

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
ggatgaagaa gatggccatc                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
aagatggcca tcggatcctc                                                  20

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 23
ctcaaytcac tcttcgagcg tc                                               22

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 24
ccatcggatc ctcaaytcac tc                                               22

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
atgaagaaga tggccatcgg                                                  20

<210> SEQ ID NO 26
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 26
```

```
ggaggatgaa gaagatgg                                                18

<210> SEQ ID NO 27
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 27
caattcgagc agctgaaa                                                18

<210> SEQ ID NO 28
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 28
ccaattcgag cagctgaaac tgcg                                         24

<210> SEQ ID NO 29
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 29
tggtgataat cggtg                                                   15

<210> SEQ ID NO 30
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 30
ctcttctggt gataatcggt gctc                                         24

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 31
ttctggtgat aatcggtgct c                                            21

<210> SEQ ID NO 32
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 32
aaccatgtca gctattatgg agctg                                        25

<210> SEQ ID NO 33
<211> LENGTH: 23
<212> TYPE: DNA
```

```
<213> ORGANISM: Artificial Sequence
<220> FEATURE:
<223> OTHER INFORMATION: Synthetic polynucleotide

<400> SEQUENCE: 33
ggtgataatc ggtgctcttg acc                                              23

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34
tctaattgtc tccctcttct g                                                21

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
attgtctccc tcttctggtg                                                  20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
gataatcggt gctcttgacc                                                  20

<210> SEQ ID NO 37
<211> LENGTH: 3569
<212> TYPE: DNA
<213> ORGANISM: Bacteriophage MS2

<400> SEQUENCE: 37
gggtgggacc cctttcgggg tcctgctcaa cttcctgtcg agctaatgcc attttttaatg      60 tctttagcga gacgctacca tggctatcgc tgtaggtagc cggaattcca ttcctaggag     120
gtttgacctg tgcgagcttt tagtacccct gatagggaga acgagacctt cgtcccctcc     180
gttcgcgttt acgcggacgg tgagactgaa gataactcat tctctttaaa atatcgttcg     240
aactggactc ccggtcgttt taactcgact ggggccaaaa cgaaacagtg gcactacccc     300
tctccgtatt cacgggggc gttaagtgtc acatcgatag atcaaggtgc ctacaagcga     360
agtgggtcat cgtggggtcg cccgtacgag gagaaagccg gtttcggctt ctccctcgac     420
gcacgctcct gctacagcct cttccctgta agccaaaact tgacttacat cgaagtgccg     480
cagaacgttg cgaaccgggc gtcgaccgaa gtcctgcaaa aggtcaccca gggtaatttt     540
aaccttggtg ttgctttagc agaggccagg tcgacagcct cacaactcgc gacgcaaacc     600
attgcgctcg tgaaggcgta cactgccgct cgtcgcggta ttggcgcca ggcgctccgc     660 taccttgccc taaacgaaga tcgaaagttt cgatcaaaac acgtggccgg caggtggttg     720
gagttgcagt tcggttggtt accactaatg agtgatatcc agggtgcata tgagatgctt     780
acgaaggttc accttcaaga gtttcttcct atgagagccg tacgtcaggt cggtactaac     840
```

```
atcaagttag atggccgtct gtcgtatcca gctgcaaact tccagacaac gtgcaacata    900
tcgcgacgta tcgtgatatg gttttacata aacgatgcac gtttggcatg gttgtcgtct    960
ctaggtatct tgaacccact aggtatagtg tgggaaaagg tgcctttctc attcgttgtc   1020
gactggctcc tacctgtagg taacatgctc gagggcctta cggcccccgt gggatgctcc   1080
tacatgtcag gaacagttac tgacgtaata acgggtgagt ccatcataag cgttgacgct   1140
ccctacgggt ggactgtgga gagacagggc actgctaagg cccaaatctc agccatgcat   1200
cgaggggtac aatccgtatg ccaacaact ggcgcgtacg taaagtctcc tttctcgatg   1260
gtccatacct tagatgcgtt agcattaatc aggcaacggc tctctagata gagccctcaa   1320
ccggagtttg aagcatggct tctaaccttta ctcagttcgt tctcgtcgac aatggcggaa   1380
ctggcgacgt gactgtcgcc ccaagcaact tcgctaacgg ggtcgctgaa tggatcagct   1440
ctaactcgcg ttcacaggct tacaaagtaa cctgtagcgt tcgtcagagc tctgcgcaga   1500
atcgcaaata caccatcaaa gtcgaggtgc ctaaagtggc aacccagact gttggtggtg   1560
tagagcttcc tgtagccgca tggcgttcgt acttaaatat ggaactaacc attccaattt   1620
tcgctacgaa ttccgactgc gagcttattg ttaaggcaat gcaaggtctc ctaaaagatg   1680
gaaacccgat tccctcagca atcgcagcaa actccggcat ctactaatag acgccggcca   1740
ttcaaacatg aggattaccc atgtcgaaga caacaaagaa gttcaactct ttatgtattg   1800
atcttcctcg cgatctttct ctcgaaattt accaatcaat tgcttctgtc gctactggaa   1860
gcggtgatcc gcacagtgac gactttacag caattgctta cttaagggac gaattgctca   1920
caaagcatcc gaccttaggt tctggtaatg acgaggcgac ccgtcgtacc ttagctatcg   1980
ctaagctacg ggaggcgaat ggtgatcgcg gtcagataaa tagagaaggt ttcttacatg   2040
acaaatcctt gtcatgggat ccggatgttt tacaaaccag catccgtagc cttattggca   2100
acctcctctc tggctaccga tcgtcgttgt ttgggcaatg cacgttctcc aacggtgctc   2160 ctatgggca caagttgcag gatgcagcgc cttacaagaa gttcgctgaa caagcaaccg   2220
ttaccccccg cgctctgaga gcggctctat tggtccgaga ccaatgtgcg ccgtggatca   2280
gacacgcggt ccgctataac gagtcatatg aatttaggct cgttgtaggg aacggagtgt   2340
ttacagttcc gaagaataat aaaatagatc gggctgcctg taaggagcct gatatgaata   2400
tgtacctcca gaaagggggtc ggtgcttttca tcagacgccg gctcaaatcc gttggtatag   2460
acctgaatga tcaatcgatc aaccagcgtc tggctcagca gggcagcgta gatggttcgc   2520
ttgcgacgat agacttatcg tctgcatccg attccatctc cgatcgcctg gtgtggagtt   2580
ttctcccacc agagctatat tcatatctcg atcgtatccg ctcacactac ggaatcgtag   2640
atggcgagac gatacgatgg gaactatttt ccacaatggg aaatgggttc acatttgagc   2700
tagagtccat gatattctgg gcaatagtca aagcgaccca aatccatttt ggtaacgccg   2760
gaaccatagg catctacggg gacgatatta tatgtcccag tgagattgca ccccgtgtgc   2820
tagaggcact tgcctactac ggttttaaac cgaatcttcg taaaacgttc gtgtccgggc   2880
tctttcgcga gagctgcggc gcgcactttt accgtggtgt cgatgtcaaa ccgttttaca   2940
tcaagaaacc tgttgacaat ctcttcgccc tgatgctgat attaaatcgg ctacggggtt   3000
ggggagttgt cggaggtatg tcagatccac gcctctataa ggtgtgggta cggctctcct   3060
cccaggtgcc ttcgatgttc ttcggtggga cggaccctcgc tgccgactac tacgtagtca   3120
gcccgcctac ggcagtctcg gtatacacca agactccgta cgggcggctg ctcgcggata   3180
```

```
cccgtacctc gggtttccgt cttgctcgta tcgctcgaga acgcaagttc ttcagcgaaa    3240
agcacgacag tggtcgctac atagcgtggt tccatactgg aggtgaaatc accgacagca    3300
tgaagtccgc cggcgtgcgc gttatacgca cttcggagtg gctaacgccg gttcccacat    3360
tccctcagga gtgtgggcca gcgagctctc ctcggtagct gaccgaggga ccccgtaaa     3420 cggggtgggt gtgctcgaaa gagcacgggt gcgaaagcgg tccggctcca ccgaaaggtg    3480
ggcgggcttc ggcccaggga cctcccccta aagagaggac ccgggattct cccgatttgg    3540
taactagctg cttggctagt taccaccca                                       3569
```

<210> SEQ ID NO 38  
<211> LENGTH: 22  
<212> TYPE: DNA  
<213> ORGANISM: Artificial Sequence  
<220> FEATURE:  
<223> OTHER INFORMATION: Synthetic polynucleotide

<400> SEQUENCE: 38

```
tggcgcgtac gtaaagtctc ct                                              22
```

<210> SEQ ID NO 39  
<211> LENGTH: 22  
<212> TYPE: DNA  
<213> ORGANISM: Artificial Sequence  
<220> FEATURE:  
<223> OTHER INFORMATION: Synthetic polynucleotide

<400> SEQUENCE: 39

```
ctggcgcgta cgtaaagtct cc                                              22
```

<210> SEQ ID NO 40  
<211> LENGTH: 25  
<212> TYPE: DNA  
<213> ORGANISM: Artificial Sequence  
<220> FEATURE:  
<223> OTHER INFORMATION: Synthetic polynucleotide

<400> SEQUENCE: 40

```
gcgcgtacgt aaagtctcct ttctc                                           25
```

<210> SEQ ID NO 41  
<211> LENGTH: 23  
<212> TYPE: DNA  
<213> ORGANISM: Artificial Sequence  
<220> FEATURE:  
<223> OTHER INFORMATION: Synthetic polynucleotide

<400> SEQUENCE: 41

```
gcattaatca ggcaacggct ctc                                             23
```

<210> SEQ ID NO 42  
<211> LENGTH: 24  
<212> TYPE: DNA  
<213> ORGANISM: Artificial Sequence  
<220> FEATURE:  
<223> OTHER INFORMATION: Synthetic polynucleotide

<400> SEQUENCE: 42

```
ccctcaaccg gagtttgaag catg                                            24
```

<210> SEQ ID NO 43  
<211> LENGTH: 19  
<212> TYPE: DNA  
<213> ORGANISM: Artificial Sequence
<220> FEATURE:
<223> OTHER INFORMATION: Synthetic polynucleotide

<400> SEQUENCE: 43
gccagttccg ccattgtcg 19

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
gtcgccagtt ccgccattgt 20

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 45
gaccccgtta gcgaagttgc 20

<210> SEQ ID NO 46
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 46
cgaccccgtt agcgaagttg 20

<210> SEQ ID NO 47
<211> LENGTH: 211
<212> TYPE: DNA
<213> ORGANISM: Influenza A virus

<400> SEQUENCE: 47
tcgtcccgtc aggccccctc aaagccgaga tcgcgcagag acttgaagat gtctttgctg 60
gaaagaacac agatcttgag gcactcatgg aatggctaaa gacaagacca atcctgtcac 120
ctttgactaa ggggatttta ggatttgtgt tcacgctcac cgtgcccagt gagcgaggac 180
tgcagcgtag acgctttgtc cagaatgccc t 211

<210> SEQ ID NO 48
<211> LENGTH: 211
<212> TYPE: DNA
<213> ORGANISM: Influenza A virus

<400> SEQUENCE: 48
tcgttccgtc aggccccctc aaagccgaga tcgcgcagag acttgaagat gtctttgctg 60
gaaagaacac agatcttgag gctctcatgg aatggctaaa gacaagacca atcctgtcac 120
ctctgactaa ggggattttg ggatttgtgt tcacgctcac cgtgcccagt gagcgaggac 180
tgcagcgtag acgctttgtc caaaatgccc t 211

<210> SEQ ID NO 49
<211> LENGTH: 211
<212> TYPE: DNA

```
<213> ORGANISM: Influenza A virus

<400> SEQUENCE: 49
tcatcccgtc aggcccctc aaagccgaga tcgcgcagag acttgaagat gtctttgcag       60
gaaagaacac tgatctcgag gctctcatgg agtggctaaa gacaagacca atcctgtcac     120
ctctgactaa agggatcttg ggatttgtgt tcacgctcac cgtgcccagt gaacgaggac     180
tgcagcgtag acgctttgtc cagaatgccc t                                    211

<210> SEQ ID NO 50
<211> LENGTH: 211
<212> TYPE: DNA
<213> ORGANISM: Influenza A virus

<400> SEQUENCE: 50
tcgtcccgtc aggcccctc aaagccgaga tcgcgcagag acttgaagat gtctttgcag       60
ggaagaacac agatctcgag gctctcatgg aatggctaaa gacaagacca atcctgtcac     120
ctttgactaa ggggattttg gggtttgtgt tcacgctcac cgtgcccagt gagcgaggac     180
tgcagcgtag acgctttgtc caaaatgcac t                                    211
```